US009480212B2

(12) United States Patent
Freeman

(10) Patent No.: US 9,480,212 B2
(45) Date of Patent: Nov. 1, 2016

(54) HYBRID CARROT VARIETY NUN 89849 CAC

(71) Applicant: Nunhems B.V., AC Nunhem (NL)

(72) Inventor: Roger Freeman, Brooks, OR (US)

(73) Assignee: Nunhems B.V., AC Nunhem (NL)

( * ) Notice: Subject to any disclaimer, the term of this patent is extended or adjusted under 35 U.S.C. 154(b) by 0 days.

(21) Appl. No.: 14/674,490

(22) Filed: Mar. 31, 2015

(65) Prior Publication Data

US 2015/0201573 A1 Jul. 23, 2015

(51) Int. Cl.
*A01H 5/06* (2006.01)
*A01H 1/02* (2006.01)
*A01H 4/00* (2006.01)

(52) U.S. Cl.
CPC .................................... *A01H 5/06* (2013.01)

(58) Field of Classification Search
CPC .................................... A01H 5/06
USPC .................................... 800/298
See application file for complete search history.

(56) References Cited

U.S. PATENT DOCUMENTS

2011/0099663 A1* 4/2011 Maxwell .................. A01H 5/06 800/268
2011/0283412 A1* 11/2011 Stelpflug .................. A01H 5/10 800/263

FOREIGN PATENT DOCUMENTS

WO 2014076249 A1 5/2014

OTHER PUBLICATIONS

Kaeppler et al (2000) Plant Molec. Biol. 43: 179-188.*
US Department of Agriculture, "Objective Description of Variety Carrot (*Daucus carota*)", ST-470-78, ams.usda.gov/AMSv1.0/getfile?dDocName=STELDEV3002673, Mar. 28, 2007.
UPOV, "Guidelines for the Conduct of Tests for Distinctness, Uniformity and Stability, TG/49/8" (Geneva 2007), http://www.upov.int/edocs/tgdocs/en/tg049.pdf.
Wijnker et al., "Hybrid Recreation by Reverse Breeding in Arabidopsis thaliana", Nature Protocols, 2014, vol. 9, No. 4, pp. 761-772.
Arnholdt-Schmitt et al., "Physiological Aspects of Genome Variability in Tissue Culture. I. Growth Phase-dependent Differential DNA Methylation of the Carrot Genome (*Daucus carota* L.) During Primary Culture", Theor Appl Genet, 1995, vol. 91, pp. 809-815.
Stein and Nothnagel, "Some Remarks on Carrot Breeding (*Daucus carota* sativus Hoffm.)", Plant Breeding, 1995, vol. 114, pp. 1-11.
Larkin and Scowcroft, "Somaclonal Variation—a Novel Source of Variability from Cell Cultures for Plant Improvement", Theor. Appl. Genet., 1981, vol. 60, pp. 197-214.
Jhang et al., "Efficiency of Different Marker Systems for Molecular Characterization of Subtropical Carrot Germplasm", Journal of Agricultural Science, 2010, vol. 148, pp. 171-181.
Shim and Jørgensen, "Genetic Structure in Cultivated and Wild Carrots (*Daucus carota* L.) Revealed by AFLP Analysis", Theor Appl Genet, 2000, vol. 101, pp. 227-233.

* cited by examiner

*Primary Examiner* — Keith Robinson

(57) ABSTRACT

The invention relates to the field of *Daucus carota*, in particular to a new variety of carrot designated NUN 89849 CAC as well as plants, seeds and carrot roots thereof.

16 Claims, No Drawings

HYBRID CARROT VARIETY NUN 89849 CAC

FIELD OF THE INVENTION

The present invention relates to the field of plant breeding. In particular, the invention provides for a new and distinct carrot variety designated NUN 89849 CAC (or "NUN 89849" or "NUN 89849 carrot" or "89849 CAC" or NUN 89849 hybrid or 89849 F1 or NUN 89849 F1 or NUN 89849 RED), and parts thereof and seeds from which the variety can be grown. The invention further relates to vegetative reproductions of NUN 89849 CAC, methods for in vitro tissue culture of NUN 89849 CAC explants and also to phenotypic variants of NUN 89849 CAC. The invention further relates to methods of producing roots of NUN 8984 CAC or of phenotypic variants of NUN 89849 CAC.

Carrot is a biennial plant that grows a rosette of leaves in the spring and summer, while building up the stout taproot, which stores large amounts of sugars for the plant to flower in the second year. The flowering stem grows several decimeters (e.g. 60-200 cm) tall, with an umbel of white flowers that produce a fruit called a mericarp.

Carrot (*Daucus carota* subsp. *sativus*), is a root vegetable, usually orange in color, though purple, red, white, cream, and yellow varieties exist. It has a crisp texture when fresh. The most commonly eaten part of a carrot is a root, although the greens are edible as well. It is a domesticated form of the wild carrot *Daucus carota*, native to Europe and southwestern Asia. The domestic carrot has been selectively bred for its greatly enlarged and more palatable, less woody-textured edible taproot. The world production of carrots and turnips for calendar year 2011 was almost 35.658 million tonnes (Food and Agriculture Organization of the United Nations (FAO)).

Vegetable breeder's aim is to combine desirable traits in a single variety. Such desirable traits may include any trait deemed beneficial by a grower and/or consumer, including greater yield, resistance to insects, disease or other pests, tolerance to environmental stress, enhanced growth rate and nutritional value.

A uniform population of a breeding line can be obtained by self-pollination and selection for type. Plants thus obtained become homozygous at almost all gene loci, i.e. a homozygous plant. Crossing two such plants of different genotypes produces a uniform population of hybrid plants that are heterozygous for many loci. On the other hand, a cross of two plants each heterozygous at a number of loci produces a population of plants that differ genetically and are not uniform. Due to this non-uniformity, performance of such plants is unpredictable.

Breeders thus prefer development of homozygous inbred plant that can be crossed to produce uniform varieties. Pedigree breeding and recurrent selection are examples of breeding methods that have been used to develop inbred plants from breeding populations. Those breeding methods combine the genetic backgrounds from two or more plants or various other broad-based sources into breeding pools from which new lines and hybrids derived therefrom are developed by selfing and selection of desired phenotypes. The new lines and hybrids are evaluated to determine which of those have commercial potential.

So far, breeding efforts have provided a number of useful carrot lines with beneficial traits, however, there remains a great need in the art for new lines with further improved traits. There is thus a need for new carrot varieties having specific combination of trait or color.

SUMMARY OF THE INVENTION

In one aspect of the invention, a seed of carrot variety NUN 89849 CAC is provided, wherein a representative sample of said seed has been deposited under Accession Number NCIMB 42394.

In another aspect the invention provides for a hybrid variety of *Daucus carota* called NUN 89849 CAC. The invention also provides for a plurality of seeds of the new variety, plants produced from growing the seeds of the new variety NUN 89849 CAC, and progeny of any of these. Especially, progeny retaining one or more (or all) of the "distinguishing characteristics" or one or more (or all) of the "essential morphological and physiological characteristics" or essentially all physiological and morphological characteristics of NUN 89849 CAC referred to herein, are encompassed herein as well as methods for producing these.

In one aspect, such progeny have all the physiological and morphological characteristics of carrot variety NUN 89849 CAC when grown under the same environmental conditions. In another aspect such progeny have all the physiological and morphological characteristics as listed in Table 1 as carrot variety NUN 89849 CAC when measured under the same environmental conditions (i.e. evaluated at significance levels of 1%, 5% or 10% significance, which can also be expressed as a p value).

In another aspect a plant of the invention or said progeny plants has/have 1, 2, 3, 4 or more or all of the distinguishing characteristics selected from the group consisting of: 1) a taproot length at market maturity of about 48.8 mm (e.g., between 46.4 and 51.2 mm); 2) root core (xylem) thickness (midpoint X-section) at market maturity of about 7.9 mm (e.g., between 7.5 and 8.3 mm); 3) medium root base type at market maturity; 4) prominent root zoning at market maturity; 5) mildly harsh root flavor at market maturity; 6) very sweet root flavor at market maturity; 7) blade length (without petiole) of about 18.6 cm (e.g., between 17.7 and 19.5 cm); 8) petiole length from crown to first pinna of about 21.3 cm (e.g., between 20.2 and 22.4 cm); 9) plant top height of about 45.4 cm (e.g., between 43.1 and 47.7 cm); and 10) plant top neck diameter of about 10.2 mm (e.g. between 9.7 and 10.7 mm). In another aspect a plant of the invention has in addition to the 1, 2, 3, 4 or more or all of the above-cited distinguishing characteristics, 3, 4, 5, 6, 7, 8, or more, or all of the other (average) characteristics as listed in Table 1.

Further, a carrot root produced on a plant grown from these seeds is provided.

In yet another embodiment of the invention, a plant having one, two or three physiological and/or morphological characteristics which are different from those of NUN 89849 CAC and which otherwise has all the physiological and morphological characteristics of NUN 89849 CAC as listed in Table 1, wherein a representative sample of seed of variety NUN 89849 CAC has been deposited under Accession Number NCIMB 42394, is provided.

Further, a vegetatively propagated plant of variety NUN 89849 CAC, or a part thereof, is provided having all the morphological and physiological characteristics of NUN 89849 CAC when grown under the same environmental conditions.

Also a plant part derived from variety NUN 89849 CAC is provided, wherein said plant part is selected from the group consisting of: root, harvested roots, parts of roots, leaf, pollen, ovule, cell, part of a leaf, petioles, shoots or parts thereof, stems or parts thereof, vines or parts thereof, roots or parts thereof, taproots, cuttings, seeds, hypocotyl, cotyledon, flowers or parts thereof, scion, cion, stock, rootstock and flower. Roots are particularly important plant parts.

DEFINITIONS

"Carrot" refers herein to plants of the species *Daucus carota*, and roots thereof.

"Cultivated carrot" refers to plants of *Daucus carota* i.e. varieties, breeding lines or cultivars of the species *D. carota* as well as crossbreds thereof, or crossbreds with other *Daucus carota* species, or ven with other *Daucus* species, cultivated by humans and having good agronomic characteristics; preferably such plants are not "wild plants", i.e. plants which generally have much poorer yields and poorer agronomic characteristics than cultivated plants and e.g. grow naturally in wild populations. "Wild plants" include for example ecotypes, PI (Plant Introduction) lines, landraces or wild accessions or wild relatives of *Daucus carota* and related species.

Refractometer % of soluable solids is the percentage of soluable solids in juice of pureed roots (mainly sugar), as defined by the USDA. It is also expressed as °Brix and indicates sweetness.

"Uniform throughout the root" or refers to a characteristics such as color being identical throughout the entire plant part (e.g. throughout the root when it is cut in half).

The terms "carrot plant designated NUN 89849 CAC", "NUN 89849" "89849 MEM" or "variety designated NUN 89849" are used interchangeably herein and refer to a carrot plant of variety NUN 89849 CAC, representative seed of said variety having been deposited under Accession Number NCIMB 42394.

"Tissue culture" refers to a composition comprising isolated cells of the same or a different type or a collection of such cells organized into parts of a plant. Tissue culture of various tissues of carrot and regeneration of plants therefrom is well known and widely published (see, e.g., Arnholdt-Schmitt et al., 1995 Theor Appl Genet (1995) 91:809-815, Larkin and Scowcroft, (1981) Theor. Appl. Genet. 60, 197-214). Similarly, the skilled person is well-aware how to prepare a "cell culture".

"UPOV descriptors" are the plant variety descriptors described for carrot in the "Guidelines for the Conduct of Tests for Distinctness, Uniformity and Stability, TG/49/8 (Geneva 2007), as published by UPOV (International Union for the Protection of New Varieties and Plants, available on the world wide web at upov.int) and which can be downloaded from the world wide web at upov.int/ under edocs/tgdocs/en/tg049.pdf and is herein incorporated by reference in its entirety.

"USDA descriptors" are the plant variety descriptors for carrot (*Daucus carota*) in the "Objective description of Variety—Carrot (*Daucus carota*)", ST-470-78, as published by U.S. Department of Agriculture, Agricultural Marketing Service, Science and Technology, Plant Variety Protection Office, Beltsville, Md. 20705 and which can be downloaded from the world wide web at ams.usda.gov/ under AMSv1.0/getfile?dDocName=STELDEV3002673.

"RHS" refers to the Royal Horticultural Society of England which publishes an official botanical color chart quantitatively identifying colors according to a defined numbering system. The chart may be purchased from Royal Horticulture Society Enterprise Ltd RHS Garden; Wisley, Woking; Surrey GU236QB, UK, e.g., the RHS colour chart: 2007 (The Royal Horticultural Society, charity No: 222879, PO Box 313 London SW1P2PE; sold by, e.g., TORSO-VERLAG, Obere Grüben 8, D-97877 Wertheim, Article-No.: Art62-00008 EAN-Nr.: 4250193402112).

As used herein, the term "plant" includes the whole plant or any parts or derivatives thereof, preferably having the same genetic makeup as the plant from which it is obtained, such as plant organs (e.g. harvested or non-harvested roots), plant cells, plant protoplasts, plant cell tissue cultures or tissue cultures from which whole plants can be regenerated, plant calli, plant cell clumps, plant transplants, seedlings, hypocotyl, cotyledon, plant cells that are intact in plants, plant clones or micropropagations, or parts of plants (e.g. harvested tissues or organs), such as plant cuttings, vegetative propagations, embryos, pollen, ovules, fruits, flowers, leaves, seeds, clonally propagated plants, roots, stems, vines, root tips, grafts, scions, rootstocks, parts of any of these and the like. Also any developmental stage is included, such as seedlings, cuttings prior or after rooting, mature plants or leaves.

"Harvested plant material" refers herein to plant parts (e.g. roots detached from the whole plant) which have been collected for further storage and/or further use.

"Harvested seeds" refers to seeds harvested from a line or variety, e.g. produced after self-fertilization or cross-fertilization and collected.

"Harvest maturity" is the time required to allow the seed to grow a root that is marketable, as described in Table 1) 3. Market Maturity—No. Days from seeding to harvest. The person skilled in the art will understand that market maturity depends on environmental conditions, such as for example soil, climate and meteorological conditions, which may include temperature, humidity, sun hours etc., and is aware how to compensate the expected harvest maturity for these factors. The time from seeding to harvest may be 1, 2, 3 or 4 weeks more or less than the value of table 1.

"Internode" refers to a portion of a plant stem or vine between nodes.

"Node" refers to the place on a plant stem or vine where a leaf is attached.

A plant having "all the physiological and morphological characteristics" of a referred-to-plant means a plant having the physiological and morphological characteristics of the referred-to-plant when grown under the same environmental conditions; the referred-to-plant can be a plant from which it was derived, e.g. the progenitor plant, the parent, the recurrent parent, the plant used for tissue- or cell culture, etc.

A plant having "essentially all the physiological and morphological characteristics" of a referred-to-plant means a plant having at least 5 (e.g. 6, 7, 8, 9 or all) of the distinguishing physiological and morphological characteristics (distinguishing characteristics as herein defined) when grown under the same environmental conditions of the referred-to-plant (e.g. a plant from which it was derived such as the progenitor plant, the parent, the recurrent parent, the plant used for tissue- or cell culture, etc.). Alternatively, a plant having "essentially all the physiological and morphological characteristics" of a referred-to-plant means a plant having all the characteristics as listed in Table 1 when grown under the same environmental conditions as a referred-to-plant (e.g. a plant from which it was derived such as the progenitor plant, the parent, the recurrent parent, the plant used for tissue- or cell culture, etc.). In another embodiment, a plant having "essentially all the physiological and morphological characteristics" of a referred-to-plant means a plant having all but 1, 2, 3, 4 or 5 of the characteristics as listed in Table 1 when grown under the same environmental conditions as a referred-to-plant (e.g. a plant from which it was derived such as the progenitor plant, the parent, the recurrent parent, the plant used for tissue- or cell culture, etc.).

For NUN 89849 CAC the distinguishing characteristics are 1) taproot length at market maturity; 2) root core (xylem) thickness (midpoint X-section) at market maturity; 3) root base type at market maturity; 4) root zoning at market maturity; 5) root flavor harshness at market maturity; 6) root flavor sweetness at market maturity; 7) blade length (without petiole); 8) petiole length from crown to first pinna; 9) plant top height; and 10) plant top neck diameter.

In certain embodiments the plant of the invention has all the physiological and morphological characteristics, except for certain characteristics mentioned, e.g. the characteristic(s) derived from a converted or introduced gene or trait and/or except for the characteristics which differ.

Similarity between different plants is defined as the number of distinguishing characteristics (or the characteristics as listed in Table 1) that are the same between the two plants that are compared when grown under the same environmental conditions. Characteristics are considered "the same" when the value for a numeric characteristic is evaluated at significance levels of 1%, 5% or 10% significance level, or when a non-numeric characteristic is identical, if the plants are grown under the same conditions.

A plant having one or more "essential physiological and/or morphological characteristics" or one or more "distinguishing characteristics" refers to a plant having (or retaining) one or more of the characteristics mentioned in Table 1 when grown under the same environmental conditions that distinguish NUN 89849 CAC from the most similar varieties (such as variety Nutri-red), such as but not limited to taproot length, root cortex thickness, root base type, zoning, flavour harshness and sweetness, blade and petiole length, plant top height, and plant top neck diameter.

"Distinguishing characteristics" or "distinguishing morphological and/or physiological characteristics" refers herein the characteristics which are distinguishing between NUN 89849 CAC and other carrot varieties, such as Nutri-Red, when grown under the same environmental conditions, especially the following characteristics 1) taproot length at market maturity of about 48.8 mm (e.g., between 46.4 and 51.2 mm); 2) root core (xylem) thickness (midpoint X-section) at market maturity of about 7.9 mm (e.g., between 7.5 and 8.3 mm); 3) medium root base at market maturity; 4) prominent root zoning at market maturity; 5) mildly harsh root flavor at market maturity; 6) very sweet root flavor at market maturity; 7) blade length (without petiole) of about 18.6 cm (e.g., between 17.7 and 19.5 cm); 8) petiole length from crown to first pinna of about 21.3 cm (e.g., between 20.2 and 22.4 cm); 9) plant top height of about 45.4 cm (e.g., between 43.1 and 47.7 cm); and 10) plant top neck diameter of about 10.2 mm (e.g. between 9.7 and 10.7 mm). In one aspect, the distinguishing characteristics further include at least one, two, three or more (or all) of the characteristics listed in Table 1. All numerical distinguishing characteristics are statistically significantly different at $p \leq 0.05$.

Thus, a carrot plant "comprising the distinguishing characteristics of NUN 89849 CAC" refers herein to a carrot plant which does not differ significantly from NUN 89849 CAC in characteristics 1) to 5) above. In a further aspect the carrot plant further does not differ significantly from NUN 89849 CAC in one or more, or all characteristics 6) to 10) as mentioned above. In yet a further aspect the carrot plant further does not differ in at least one, two, three, four, five or six (or all) characteristics selected from the characteristics listed in Table 1. In still another aspect the carrot plant does not differ in any of the distinguishing characteristics 1) to 10) listed above.

The physiological and/or morphological characteristics mentioned above are commonly evaluated at significance levels of 1%, 5% or 10% if they are numerical, or for identical type if not numerical, when measured under the same environmental conditions. For example, a progeny plant of NUN 89849 CAC may have one or more (or all) of the essential physiological and/or morphological characteristics of NUN 89849 CAC listed in Table 1, as determined at the 5% significance level (i.e. $p \leq 0.05$) when grown under the same environmental conditions.

As used herein, the term "variety" or "cultivar" means a plant grouping within a single botanical taxon of the lowest known rank, which grouping, irrespective of whether the conditions for the grant of a breeder's right are fully met, can be defined by the expression of the characteristics resulting from a given genotype or combination of genotypes, distinguished from any other plant grouping by the expression of at least one of the said characteristics and considered as a unit with regard to its suitability for being propagated unchanged.

"Plant line" is for example a breeding line which can be used to develop one or more varieties. Progeny obtained by selfing a plant line has the same phenotype as its parents.

"Hybrid variety" or "F1 hybrid" refers to the seeds harvested from crossing two inbred (nearly homozygous) parental lines. For example, the female parent is pollinated with pollen of the male parent to produce hybrid (F1) seeds on the female parent.

"Regeneration" refers to the development of a plant from cell culture or tissue culture or vegetative propagation.

"Vegetative propagation", "vegetative reproduction" or "clonal propagation" are used interchangeably herein and mean the method of taking part of a plant and allowing that plant part to form at least roots where plant part is, e.g., defined as or derived from (e.g. by cutting of) leaf, pollen, embryo, cotyledon, hypocotyl, cells, protoplasts, meristematic cell, root, taproot, root tip, pistil, anther, flower, shoot tip, shoot, stem, vines, fruit, petiole, etc. When a whole plant is regenerated by vegetative propagation, it is also referred to as a vegetative propagation.

"Planting" or "planted" refers to seeding (direct sowing) or transplanting seedlings (plantlets) into a field by machine or hand.

"Yield" means the total weight of all carrot roots harvested per hectare of a particular line or variety. It is understood that "yield" expressed as weight of all carrot roots harvested per hectare can be obtained by multiplying the number of plants per hectare times the "yield per plant".

"Marketable yield" means the total weight of all marketable carrot roots harvested per hectare of a particular line or variety, i.e. roots suitable for being sold for fresh consumption or processing, having good top growth, acceptable length, uniformity and core diameter, a rich color, good brix and flavor and no or very low levels of deficiencies.

"Selfing" refers to self-pollination of a plant, i.e., the transfer of pollen from the anther to the stigma of the same plant. "Crossing" refers to the mating of two parent plants.

"Average" refers herein to the arithmetic mean.

The term "about" in relation to a particular value refers to said value +/−5%, i.e. to a range between said value minus 5% of said value and said value plus 5% of said value.

"Substantially equivalent" refers to a characteristic that, when compared, does not show a statistically significant difference (e.g., p=0.05) from the mean. ANOVA is a suitable method for determining the value of p.

"Locus" (plural loci) refers to the specific location of a gene or DNA sequence on a chromosome. A locus may confer a specific trait.

"Allele" refers to one or more alternative forms of a gene locus. All of these loci relate to one trait. Sometimes, different alleles can result in different observable phenotypic traits, such as different pigmentation. However, many variations at the genetic level result in little or no observable variation. If a multicellular organism has two sets of chromosomes, i.e. diploid, these chromosomes are referred to as homologous chromosomes. Diploid organisms have one copy of each gene (and therefore one allele) on each chromosome. If both alleles are the same, they are homozygotes. If the alleles are different, they are heterozygotes.

"Genotype" refers to the genetic composition of a cell or organism.

"Flavor" refers to the sensory impression of a food or other substance, especially a carrot root or root part (root flesh) and is determined mainly by the chemical senses of taste and smell. Flavor is influenced by texture properties and by volatile and/or non-volatile chemical components (organic acids, lipids, carbohydrates, etc.).

The term "traditional breeding techniques" encompasses herein crossing, selfing, selection, double haploid production, embryo rescue, protoplast fusion, marker assisted selection, mutation breeding etc. as known to the breeder (i.e. methods other than genetic modification/transformation/transgenic methods), by which, for example, a genetically heritable trait can be transferred from one carrot line or variety to another.

"Backcrossing" is a traditional breeding technique used to introduce a trait into a plant line or variety. The plant containing the trait is called the donor plant and the plant into which the trait is transferred is called the recurrent parent. An initial cross is made between the donor parent and the recurrent parent to produce progeny plants. Progeny plants which have the trait are then crossed to the recurrent parent. After several generations of backcrossing and/or selfing the recurrent parent comprises the trait of the donor. The plant generated in this way may be referred to as a "single trait converted plant".

"Progeny" as used herein refers to plants derived from a plant designated NUN 89849 CAC. Progeny may be derived by regeneration of cell culture or tissue culture or parts of a plant designated NUN 89849 CAC or selfing of a plant designated NUN 89849 CAC or by producing seeds of a plant designated NUN 89849 CAC. In further embodiments, progeny may also encompass plants derived from crossing of at least one plant designated NUN 89849 CAC with another carrot plant of the same or another variety or (breeding) line, or wild carrot plants, backcrossing, inserting of a locus into a plant or mutation. A progeny is, e.g., a first generation progeny, i.e. the progeny is directly derived from, obtained from, obtainable from or derivable from the parent plant by, e.g., traditional breeding methods (selfing and/or crossing) or regeneration. However, the term "progeny" generally encompasses further generations such as second, third, fourth, fifth, sixth, seventh or more generations, i.e., generations of plants which are derived from, obtained from, obtainable from or derivable from the former generation by, e.g., traditional breeding methods, regeneration or genetic transformation techniques. For example, a second generation progeny can be produced from a first generation progeny by any of the methods mentioned above.

The terms "gene converted" or "conversion plant" in this context refer to carrot plants which are developed by backcrossing wherein essentially all of the desired morphological and physiological characteristics of parent are recovered in addition to the one or more genes transferred into the parent via the backcrossing technique or via genetic engineering. Likewise a "Single Locus Converted (Conversion) Plant" refers to plants which are developed by plant breeding techniques comprising or consisting of backcrossing, wherein essentially all of the desired morphological and physiological characteristics of a carrot variety are recovered in addition to the characteristics of the single locus having been transferred into the variety via the backcrossing technique and/or by genetic transformation.

"Transgene" or "chimeric gene" refers to a genetic locus comprising a DNA sequence which has been introduced into the genome of a carrot plant by transformation. A plant comprising a transgene stably integrated into its genome is referred to as "transgenic plant".

The term "mean" refers to the arithmetic mean of several measurements. The skilled person understands that the appearance of a plant depends to some extent on the growing conditions of said plant. Thus, the skilled person will know typical growing conditions for carrots described herein. The mean, if not indicated otherwise within this application, refers to the arithmetic mean of measurements on at least 10 different, randomly selected plants of a variety or line.

"Substantially equivalent" refers to a characteristic that, when compared, does not show a statistically significant difference (e.g., p>0.05) from the mean.

DETAILED DESCRIPTION

The present invention relates to a *Daucus carota* variety, referred to as NUN 89849 CAC, which—when compared to check variety Nutri-Red—has a longer taproot at market at market maturity (than check variety Nutri-Red), a thicker root cortex at market maturity (than check variety Nutri-Red); a medium root base type at market maturity (as compared to a pointed root base of check variety Nutri-Red), prominent root zoning at market maturity (as compared to a faint root zoning of check variety Nutri-Red), a mildly harsh root flavor at market maturity (as compared to the very harsh root flavor of check variety Nutri-Red), shorter blades (than check variety Nutri-Red), shorter petioles (than check variety Nutri-Red), a shorter plant at top height (than check variety Nutri-Red), and smaller plant top neck diameter (than check variety Nutri-Red). Also encompassed by the present invention are progeny plants having all but 1, 2, or 3 of the morphological and/ physiological characteristics of NUN 89849 CAC and methods of producing plants in accordance with the present invention.

A carrot plant of NUN 89849 CAC differs from the most similar comparison variety Nutri-Red in one or more characteristics (referred herein to as "distinguishing characteristics" or "distinguishing morphological and/or physiological characteristics" (or essential physiological and/or morphological characteristics) selected from:

1) NUN 89849 CAC has a taproot at market maturity that is at least 50%, 60%, 70%, 80%, 90%, 100% or even 100.8% longer than the taproot of check variety Nutri-Red;
2) NUN 89849 CAC has a root core at market maturity that is at least 7%, 10%, 15%, 20%, 21%, or even 21.5% thicker than the core of check variety Nutri-Red;

3) NUN 89849 CAC has medium root base type at market maturity as compared to the pointed root base of check variety Nutri-Red;
4) NUN 89849 CAC has prominent root zoning at market maturity as compared to the faint root zoning of check variety Nutri-Red
5) NUN 89849 CAC has a mildly harsh root flavour at market maturity as compared to the very harsh flavour of check variety Nutri-Red
6) NUN 89849 CAC has very sweet root flavour at market maturity as compared to the not sweet flavour of check variety Nutri-Red
7) NUN 89849 CAC has blades that are at least 5%, 10%, 15%, 20%, 22%, or even 22.2% shorter than the blades of check variety Nutri-Red;
8) NUN 89849 CAC has petioles that are at least 5%, 10%, 15%, 20%, 21%, or even 21.7% shorter than the petioles of check variety Nutri-Red;
9) NUN 89849 CAC has a plant at top height that is at least 5%, 7%, 9%, 10%, 14%, or even 14.7% shorter that the plant at top height of check variety Nutri-Red;
10) NUN 89849 CAC has a plant top neck diameter that is at least 25%, 30%, 40%, 45% or even 45.7% smaller than the plant top neck diameter of check variety Nutri-Red.

In another embodiment the plant of the invention has a leaf petiole diameter that is at least 15%, 20%, 25%, or even 25.2% smaller than the petiole diameter of check variety Nutri-Red.

It is understood that "significant" differences refer to statistically significant differences, when comparing the characteristic between two plant lines or varieties when grown under the same conditions. Preferably at least about 10, 15, 20 or more plants per line or variety are grown under the same conditions (i.e. side by side) and characteristics are measured on at least about 10, 15, 20 or more randomly selected plant or plant parts to obtain averages. Thus, physiological and morphological characteristics or traits are commonly evaluated at a significance level of 1%, 5% or 10%, when measured in plants grown under the same environmental conditions.

Thus, in one aspect, the invention provides seeds of the carrot variety designated NUN 89849 CAC wherein a representative sample of seeds of said variety was deposited under the Budapest Treaty, with Accession number NCIMB 42394.

Seeds of NUN 89849 CAC are obtainable by crossing the male parent with the female parent and harvesting the seeds produced on the female parent. The resultant NUN 89849 CAC seeds can be grown to produce NUN 89849 CAC plants. In one embodiment a plurality of NUN 89849 CAC seeds are packaged into small and/or large containers (e.g., bags, cartons, cans, etc.). The seeds may be disinfected, primed and/or treated with various compounds, such as seed coatings or crop protection compounds.

Also provided are plants of carrot variety NUN 89849 CAC, or a root or other plant part thereof, produced from seeds, wherein a representative sample of said seeds has been deposited under the Budapest Treaty, with Accession Number NCIMB 42394. Also included is a cell culture or tissue culture produced from such a plant. It is understood that such tissue or cell culture comprising cells or protoplasts from the plant of the invention can be obtained from a plant part selected from the group consisting of embryos, meristems, cotyledons, hypocotyl, pollen, leaves, anthers, roots, root tips, pistil, petiole, flower, fruit, seed, stem and stalks. In one embodiment a plant regenerated from such a cell or tissue culture said plant expressing all the morphological and physiological characteristics of NUN 89849 CAC.

In one embodiment the invention provides a carrot plant regenerated from the tissue or cell culture of NUN 89849 CAC, wherein the plant has all of the physiological and morphological characteristics of NUN 89849 CAC as listed in Table 1 when determined at the 5% significance level. In another embodiment, the invention provides a carrot plant regenerated from the tissue or cell culture of NUN 89849 CAC, wherein the plant has all of the physiological and morphological characteristics of NUN 89849 CAC when determined at the 5% significance level.

Plants of NUN 89849 CAC can be produced by seeding directly in the ground (e.g., field) or by germinating the seeds in controlled environment conditions (e.g., greenhouses) and then transplanting the seedlings into the field. For example, the seed can be sown into prepared seed beds where they will remain for the entire production of the crop. Alternatively, the carrot seed may be planted or transplanted in prepared mounds.

In another aspect, the invention provides for a carrot plant of variety NUN 89849 CAC, a representative sample of seed from said variety has been deposited under the Budapest Treaty, with Accession number NCIMB 42394.

In other aspects, the invention provides for a root or parts thereof of carrot variety NUN 89849 CAC, or a plant part, such as pollen, flowers, shoots or cuttings of variety NUN 89849 CAC or parts thereof.

In one embodiment any plant of the invention comprises at least 3, 4, 5 or more, e.g. 6, 7, 8, 9 or all of the following morphological and/or physiological characteristics (i.e. distinguishing characteristics (average values; measured at harvest or market maturity, as indicated on the USDA Objective description of variety—Carrot (unless indicated otherwise), when grown under the same environmental conditions):

1) NUN 89849 CAC has a taproot length at market maturity of about 48.8 mm, that is between 25 and 70 mm, or between 30 and 65 mm, or between 40 and 57 mm, or between 47 and 50 mm, or between 48 and 49 mm, or even between 48.7 and 48.9 mm;
2) NUN 89849 CAC has a root core (xylem) thickness (midpoint X-section) at market maturity of about 7.9 mm, that is between 6.8 and 8.7 mm, or between 7.5 and 8.5 mm, or between 7 and 8 mm, or even between 7.8 and 8.0 mm;
3) NUN 89849 CAC has a medium root base type at market maturity;
4) NUN 89849 CAC has a prominent root zoning at market maturity;
5) NUN 89849 CAC has mildly harsh root flavor at market maturity;
6) NUN 89849 CAC has very sweet root flavor at market maturity;
7) NUN 89849 CAC has a blade length of about 18.6 cm, that is between 15 and 22 cm, or between 17 and 20 cm, or between 18 and 19 cm, or even between 18.5 and 18.7 cm;
8) NUN 89849 CAC has a petiole length of about 21.3 cm, that is between 16 and 27 cm, or between 18 and 25 cm or between 21 and 22 cm, or even between 21.2 and 21.4 cm;
9) NUN 89849 CAC has a plant top height of about 45.4 cm, that is between 38 and 53 cm, or between 41 and 50 cm, or between 44 and 47 cm, or between 45 and 46 cm, or even between 45.3 and 45.5 cm; and, 10) NUN 89849 CAC has a plant top neck diameter of about 10.2 mm, that is between and 3 and 18 mm, or between 7 and 14 mm, or between 9 and 12 mm, or between 10 and 11 mm, or even between 10.1 and 10.3 mm.

In another embodiment the plant of the invention has an average leaf petiole diameter that is about 3.5 mm, that is between 2.5 and 4.5 mm, or between 3 and 4 mm, or even between 3.4 and 3.6 mm.

In still another aspect the invention provides a method of producing a carrot plant, comprising crossing a plant of carrot variety NUN 89849 CAC with a second carrot plant one or more times, and selecting progeny from said crossing.

In yet another aspect the invention provides a method of producing a carrot plant, comprising selfing a plant of carrot variety NUN 89849 CAC one or more times, and selecting progeny from said selfing.

In other aspects, the invention provides for progeny of variety NUN 89849 CAC such as progeny obtained by further breeding NUN 89849 CAC. Further breeding NUN 89849 CAC includes selfing NUN 89849 CAC one or more times and/or cross-pollinating NUN 89849 CAC with another carrot plant or variety one or more times. In particular, the invention provides for progeny that retain all the essential morphological and physiological characteristics of NUN 89849 CAC or that retain one or more (e.g. 1) to 4) or 1) to 7) or all) of the distinguishing characteristics of the carrot type described further above, or, in another embodiment, progeny that retain all morphological and physiological characteristics of NUN 89849 CAC as listed in Table 1; when grown under the same environmental conditions, when determined at the 5% significance level. In another aspect, the invention provides for vegetative reproductions of the variety and plants having all but 1, 2, or 3 of the physiological and morphological characteristics of NUN 89849 CAC (e.g. as listed in Table 1).

The morphological and/or physiological differences between plants according to the invention, i.e. NUN 89849 CAC or progeny thereof, or plants having all but 1, 2, or 3 of the physiological and morphological characteristics of NUN 89849 CAC (as listed in Table 1); and other known varieties can easily be established by growing NUN 89849 CAC next to the other varieties (in the same field, under the same environmental conditions), preferably in several locations which are suitable for said carrot cultivation, and measuring morphological and/or physiological characteristics of a number of plants (e.g., to calculate an average value and to determine the variation range/uniformity within the variety). For example, trials can be carried out in El Centro Calif., USA (N 32 degrees 74'520"/W 115 degrees 37'179", USA, whereby type, region of adaptation, maturity, plant top dimensions, root length, root diameter, root shape, root color, root surface, taproot length, leaf shape, leaf color, disease resistance, insect resistance and physiological reactions can be measured and directly compared for species of *Daucus carota.*

The morphological and physiological characteristics (and distinguishing characteristics) of NUN 89849 CAC, are provided in the Examples, in Table 1. Encompassed herein are also plants derivable from NUN 89849 CAC (e.g. by selfings and/or crossing and/or backcrossing with NUN 89849 CAC and/or progeny thereof) comprising all the physiological and morphological characteristics of NUN 89849 CAC listed in Table 1 as determined at the 5% significance level for numerical characteristics or identical for non-numerical characteristics when grown under the same environmental conditions and/or comprising one or more (or all; or all except one, two or three) of the distinguishing characteristics as determined at the 5% significance level when grown under the same environmental conditions.

Also at-harvest and/or post-harvest characteristics of roots can be compared, such as cold storage holding quality, post-harvest rind firmness and/or flesh firmness can be measured using known methods.

The morphological and/or physiological characteristics may vary somewhat with variation in the environment (such as temperature, light intensity, day length, humidity, soil, fertilizer use), which is why a comparison under the same environmental conditions is preferred. Colors can best be measured against The Munsell Book of Color (Munsell Color Macbeth Division of Kollmorgan Instruments Corporation) or using the Royal Horticultural Society Chart (World wide web at rhs.org.uk/Plants/RHS-Publications/RHS-colour-charts).

In a preferred embodiment, the invention provides for carrot roots of variety NUN 89849 CAC, or a part of the root. In another embodiment, the invention provides for a container comprising or consisting of a plurality of harvested carrot roots of NUN 89849 CAC, or progeny thereof, or a derived variety.

In yet a further embodiment, the invention provides for a method of producing a new carrot plant. The method comprises crossing a plant of the invention NUN 89849 CAC, or a plant comprising all but 1, 2, or 3 of the morphological and physiological characteristics of NUN 89849 CAC (as listed in Table 1), or a progeny plant thereof, either as male or as female parent, with a second carrot plant (or a wild relative of carrot) one or more times, and/or selfing a carrot plant according to the invention i.e. NUN 89849 CAC, or a progeny plant thereof, one or more times, and selecting progeny from said crossing and/or selfing. The second carrot plant may for example be a line or variety of the species *Daucus carota*, or other *Daucus* species or even other *Apiaceae* species.

Progeny are a later generation (of seeds) produced from the first cross of the F1 hybrid with another plant (F2) or with itself (S2), or any further generation produced by crossing and/or selfing (F3, F4, etc.) and/or backcrossing (BC2, BC3, etc.) one or more selected plants of the F2 and/or S2 and/or BC2 generation (or plants of any further generation, e.g. the F3) with another carrot plant (and/or with a wild relative of carrot). Progeny may have all the physiological and morphological characteristics of carrot variety NUN 89849 CAC when grown under the same environmental conditions and/or progeny may have (be selected for having) one or more of the distinguishing characteristics of carrot of the invention. Using common breeding methods such as backcrossing or recurrent selection, one or more specific characteristics may be introduced into NUN 89849 CAC, to provide or a plant comprising all but 1, 2, or 3 or more of the morphological and physiological characteristics of NUN 89849 CAC (as listed in Table 1).

The invention provides for methods of producing plants which retain all the morphological and physiological characteristics of NUN 89849 CAC. The invention provides also for methods of producing a plant comprising all but 1, 2, or 3 or more of the morphological and physiological characteristics of NUN 89849 CAC (e.g. as listed in Table 1), but which are still genetically closely related to NUN 89849 CAC. The relatedness can, for example be determined by fingerprinting techniques (e.g., making use of isozyme markers and/or molecular markers such as SNP markers, AFLP markers, microsatellites, minisatellites, RAPD markers, RFLP markers and others). A plant is "closely related" to NUN 89849 CAC if its DNA fingerprint is at least 80%, 90%, 95% or 98% identical to the fingerprint of NUN 89849 CAC. In a preferred embodiment AFLP markers are used for DNA fingerprinting (Shim and Jørgensen, Theor Appl Genet (2000) 101:227-233). A closely related plant may have a Jaccard's Similarity index of at least about 0.8, preferably at least about 0.9, 0.95, 0.98 or more (Jhang et al., J. Agricultural Sci. 2010-Vol 148 (2) pp 171-181). The invention also provides plants and varieties obtained by these methods. Plants may be produced by crossing and/or selfing, or alternatively, a plant may simply be identified and selected amongst NUN 89849 CAC plants, or progeny thereof, e.g. by identifying a variant within NUN 89849 CAC or progeny thereof (e.g. produced by selfing) which variant differs from NUN 89849 CAC in one, two or three of the morphological and/or physiological characteristics (e.g. in one, two or three distinguishing characteristics), e.g. those listed in Table 1 or others. In one embodiment the invention provides a carrot plant having a Jaccard's Similarity index with NUN 89849 CAC of at least 0.8, e.g. at least 0.85, 0.9, 0.95, 0.98 or even at least 0.99.

By crossing and/or selfing also (one or more) single traits may be introduced into the variety of the invention i.e. NUN 89849 CAC (e.g., using backcrossing breeding schemes), while retaining the remaining morphological and physiological characteristics of NUN 89849 CAC and/or while retaining one or more distinguishing characteristics. A single trait converted plant may thereby be produced. For example, disease resistance genes may be introduced, genes responsible for one or more quality traits, yield, etc. Both single genes (dominant or recessive) and one or more QTLs (quantitative trait loci) may be transferred into NUN 89849 CAC by breeding with NUN 89849 CAC.

Any pest or disease resistance genes may be introduced into a plant according to the invention. NUN 98849 CAC, progeny thereof or into a plant comprising all but 1, 2, or 3 or more of the morphological and physiological characteristics of NUN 98849 CAC (e.g. as listed in Table 1). Resistance to one or more of the following diseases or pests is preferably introduced into plants of the invention: *Alternaria* Blight, Aster Yellows, Cavity Spot, *Cercospora* Blight, Motley Dwarf Virus, Powdery Mildew, *Pythium* Root Dieback, *Schlerotinia* Decay and Root Knot (Nematode). Other resistance genes, against pathogenic viruses, fungi, bacteria, nematodes, insects or other pests may also be introduced, as well as resistance to physiological reactions. In an embodiment, NUN 98849 CAC is resistant to Bolting and Root splitting.

Thus, invention also provides a method for developing a carrot plant in a carrot breeding program, using a carrot plant of the invention, or its parts as a source of plant breeding material. Suitable plant breeding techniques are recurrent selection, backcrossing, pedigree breeding, mass selection, mutation breeding and/or genetic marker enhanced selection. For example, in one aspect, the method comprises crossing NUN 89849 CAC or progeny thereof, or a plant comprising all but 1, 2, or 3 or more of the morphological and physiological characteristics of NUN 89849 CAC (e.g. as listed in Table 1), with a different carrot plant, and wherein one or more offspring of the crossing are subject to one or more plant breeding techniques selected from the group consisting of recurrent selection, backcrossing, pedigree breeding, mass selection, mutation breeding and genetic marker enhanced selection (see e.g. Stein and Nothnagel, (1995) Plant Breeding 114, 1-11). For breeding methods in general see Principles of Plant Genetics and Breeding, 2007, George Acquaah, Blackwell Publishing, ISBN-13: 978-1-4051-3646-4.

The invention thus also provides a method of introducing a single locus conversion, or single trait conversion or introducing a desired trait, into a carrot plant according to the invention and/or into NUN 89849 CAC comprising:

(a) crossing a carrot plant of variety NUN 89849 CAC, a representative sample of seed of said variety having been deposited under Accession Number NCIMB 42394, with a second carrot plant comprising a desired single locus to produce F2 progeny plants;

(b) selecting F2 progeny plants that have the single locus;

(c) crossing the selected progeny plants with a plant of NUN 89849 CAC, to produce backcross progeny plants;

(d) selecting backcross progeny plants that have the single locus and one or more (or all) distinguishing characteristics of carrot according to the invention and/or all the physiological and morphological characteristics of NUN 89849 CAC to produce selected backcross progeny plants; and (e) optionally repeating steps (c) and (d) one or more times in succession to produce selected second, third or fourth or higher backcross progeny plants that comprise the single locus and otherwise one or more (or all) the distinguishing characteristics of the carrots according to the invention and/or comprise all of the physiological and morphological characteristics of NUN 89849 CAC, when grown in the same environmental conditions. The invention further relates to plants obtained by this method.

The above method is provided, wherein the single locus confers a trait, wherein the trait is pest resistance or disease resistance.

In one embodiment the trait is disease resistance and the resistance is conferred to *Alternaria* Blight, Aster Yellows, Cavity Spot, *Cercospora* Blight, Motley Dwarf Virus, Powdery Mildew, *Pythium* Root Dieback and *Schlerotinia* Decay.

The invention also provides a carrot plant comprising at least a first set of the chromosomes of carrot variety NUN 89849 CAC, a sample of seed of said variety having been deposited under Accession Number NCIMB 42394; optionally further comprising a single locus conversion, wherein said plant has essentially all of the morphological and physiological characteristics of the plant comprising at least a first set of the chromosomes of carrot NUN 89849 CAC. In another embodiment, this single locus conversion confers a trait selected from the group consisting of male sterility, herbicide tolerance, insect resistance, pest resistance, disease resistance, environmental stress tolerance, modified carbohydrate metabolism and modified protein metabolism.

In one embodiment, NUN 89849 CAC may also be mutated (by e.g. irradiation, chemical mutagenesis, heat treatment, etc.) and mutated seeds or plants may be selected in order to change one or more characteristics of NUN 89849 CAC. Methods such as TILLING may be applied to carrot populations in order to identify mutants. Similarly, NUN 89849 CAC may be transformed and regenerated, whereby one or more chimeric genes are introduced into the variety or into a plant comprising all but 1, 2, 3, or more of the morphological and physiological characteristics (e.g. as listed in Table 1). Transformation can be carried out using standard methods, such as *Agrobacterium tumefaciens* mediated transformation or biolistics, followed by selection of the transformed cells and regeneration into plants. A desired trait (e.g. genes conferring pest or disease resistance, herbicide, fungicide or insecticide tolerance, etc.) can be introduced into NUN 89849 CAC, or progeny thereof, by transforming NUN 89849 CAC or progeny thereof with a transgene that confers the desired trait, wherein the transformed plant retains all the phenotypic and/or morphological and/or physiological characteristics of NUN 89849 CAC or the progeny thereof and contains the desired trait.

The invention also provides for progeny of hybrid (F1) variety NUN 89849 CAC obtained by further breeding with NUN 89849 CAC. In one aspect progeny are F2 progeny obtained by crossing NUN 89849 CAC with another plant or S2 progeny obtained by selfing NUN 89849 CAC. Also encompassed are F3 progeny obtained by selfing the F2 plants. “Further breeding” encompasses traditional breeding (e.g., selfing, crossing, backcrossing), marker assisted breeding, and/or mutation breeding. In one embodiment, the progeny have one or more (or all) of the distinguishing characteristics mentioned further above when grown under the same environmental conditions. In a further embodiment the progeny have all the physiological and morphological characteristics of variety NUN 89849 CAC when grown under the same environmental conditions. In another embodiment the progeny have one, two, or three distinct traits (qualitative or quantitative) introduced into NUN 89849 CAC, while retaining all the other physiological and morphological characteristics of variety NUN 89849 CAC when grown under the same environmental conditions.

The invention also provides a plant having one, two or three physiological and/or morphological characteristics which are different from those of NUN 89849 CAC and which otherwise has all the physiological and morphological characteristics of NUN 89849 CAC, wherein a representative sample of seed of variety NUN 89849 CAC has been deposited under Accession Number NCIMB 42394. In particular plants which differ from NUN 89849 CAC in none, one, two or three of the characteristics mentioned in Table 1 are encompassed.

In one aspect, the plant having one, two or three physiological and/or morphological characteristics which are different from those of NUN 89849 CAC and which otherwise has all the physiological and morphological characteristics of NUN 89849 CAC differs from NUN 89849 CAC in one, two or three of the distinguishing morphological and/or physiological characteristics selected from 1) average taproot length at market maturity; 2) average root core (xylem) thickness (midpoint X-section) at market maturity; 3) root base type at market maturity; 4) root zoning at market maturity; 5) root flavor harshness at market maturity; 6) root flavor sweetness at market maturity; 7) average blade length (without petiole); 8) average petiole length from crown to first pinna; 9) average plant top height; and 10) average plant top neck diameter.

In another embodiment the plant having one, two or three physiological and/or morphological characteristics which are different from those of NUN 89849 CAC and which otherwise has all the physiological and morphological characteristics of NUN 89849 CAC differs from NUN 89849 CAC in one, two or three morphological or physiological characteristic other than the “distinguishing morphological and/or physiological characteristics” (or essential physiological and/or morphological characteristics) of NUN 89849 CAC selected from 1) average taproot length at market maturity; 2) average root core (xylem) thickness (midpoint X-section) at market maturity; 3) root base type at market maturity; 4) root zoning at market maturity; 5) root flavor harshness at market maturity; 6) root flavor sweetness at market maturity; 7) average blade length (without petiole); 8) average petiole length from crown to first pinna; 9) average plant top height; and 10) average plant top neck diameter.

Carrots according to the invention, such as the variety NUN 89849 CAC, or its progeny, or a plant having all physiological and/or morphological characteristics but one, two or three which are different from those of NUN 89849 CAC, can also be reproduced using vegetative reproduction methods. Therefore, the invention provides for a method of producing plants, or a part thereof, of variety NUN 89849 CAC, comprising vegetative propagation of variety NUN 89849 CAC. Vegetative propagation comprises regenerating a whole plant from a plant part of variety NUN 89849 CAC (or from its progeny or from or a plant having all physiological and/or morphological characteristics but one, two or three, which are different from those of NUN 89849 CAC), such as a cutting, a cell culture or a tissue culture.

The invention also concerns methods of vegetatively propagating a plant of the invention. In certain embodiments, the method comprises the steps of: (a) collecting tissue or cells capable of being propagated from a plant of the invention; (b) cultivating said tissue or cells to obtain proliferated shoots; and (c) rooting said proliferated shoots, to obtain rooted plantlets. Steps (b) and (c) may also be reversed, i.e. first cultivating said tissue to obtain roots and then cultivating the tissue to obtain shoots, thereby obtaining rooted plantlets. The rooted plantlets may then be further grown, to obtain plants. In one embodiment, the method further comprises step (d) growing plants from said rooted plantlets The invention also provides for a vegetatively propagated plant of variety NUN 89849 CAC (or from its progeny or from or a plant having all but one, two or three physiological and/or morphological characteristics which are different from those of NUN 89849 CAC, or a part thereof, having one or more distinguishing characteristics and/or all the morphological and physiological characteristics of NUN 89849 CAC (except for the characteristics differing), when grown under the same environmental conditions.

Parts of NUN 89849 CAC (or of its progeny or of a plant having all physiological and/or morphological characteristics but one, two or three which are different from those of NUN 89849 CAC) encompass any cells, tissues, organs obtainable from the seedlings or plants, such as but not limited to: carrot roots or parts thereof, cuttings, hypocotyl, cotyledon, pollen, scion and the like. Such parts can be stored and/or processed further. Encompassed are therefore also food or feed products comprising one or more of such parts, such as canned, chopped, cooked, roasted, preserved, frozen, dried, pickled, or juiced carrot root from NUN 89849 CAC or from progeny thereof, or from a derived variety, such as a plant having all but one, two or three physiological and/or morphological characteristics which are different from those of NUN 89849 CAC.

In one aspect haploid plants and/or double haploid plants of NUN 89849 CAC, or a plant having all but one, two or three physiological and/or morphological characteristics which are different from those of NUN 89849 CAC, or progeny of any of these, are encompassed herein. Haploid and double haploid (DH) plants can, for example, be produced by cell or tissue culture and chromosome doubling agents and regeneration into a whole plant. For DH production chromosome doubling may be induced using known methods, such as colchicine treatment or the like.

Also provided are plant parts derived from variety NUN 89849 CAC (or from its progeny or from a plant having all but one, two or three physiological and/or morphological characteristics which are different from those of NUN 89849 CAC), or from a vegetatively propagated plant of NUN 89849 CAC (or from its progeny or from a plant having all but one, two or three physiological and/or morphological characteristics which are different from those of NUN 89849

CAC), being selected from the group consisting of: harvested roots or parts thereof, pollen, cells, leaves or parts thereof, petioles, cotyledons, hypocotyls, shoots or parts thereof, stems or parts thereof, or vines or parts thereof, roots or parts thereof, cuttings, or flowers.

In one embodiment, the invention provides for extracts of a plant described herein and compositions comprising or consisting of such extracts. In a preferred embodiment, the extract consists of or comprises tissue of a plant described herein or is obtained from such tissue.

In still yet another aspect, the invention provides a method of determining the genotype of a plant of the invention comprising detecting in the genome (e.g., a sample of nucleic acids) of the plant at least a first polymorphism. The method may, in certain embodiments, comprise detecting a plurality of polymorphisms in the genome of the plant, for example by obtaining a sample of nucleic acid from a plant and detecting in said nucleic acids a plurality of polymorphisms. The method may further comprise storing the results of the step of detecting the plurality of polymorphisms on a computer readable medium The invention also provides for a food or feed product comprising or consisting of a plant part described herein wherein the plant part can be identified as a part of the plant of the invention. Preferably, the plant part is a carrot root or part thereof and/or an extract from a root or another plant part described herein. The food or feed product may be fresh or processed, e.g., dried, grinded, powdered, pickled, chopped, cooked, juiced, preserved, pickled, or powdered canned, steamed, boiled, blanched and/or frozen, etc.

For example, containers such as cans, boxes, crates, bags, cartons, Modified Atmosphere Packagings, films (e.g. biodegradable films), etc. comprising plant parts of plants (fresh and/or processed) described herein are also provided herein.

Marketable carrot roots are generally sorted by size and quality after harvest. Alternatively the carrot roots can be sorted by Brix or sugar content.

Carrots may also be grown for use in grafting or inosculation as rootstocks (stocks) or scions (scions). Typically, different types of carrots are grafted to enhance disease resistance, which is usually conferred by the rootstock, while retaining the horticultural qualities usually conferred by the scion. It is not uncommon for grafting to occur between cultivated carrot varieties and related *Daucus* species. Methods of grafting and vegetative propagation are well-known in the art.

So in one aspect the invention relates to a plant comprising a rootstock or scion of NUN 89849 CAC.

Using methods known in the art like “reverse breeding”, it is possible to produce parental lines for a hybrid plant such as NUN 89849 CAC; where normally the hybrid is produced from the parental lines. Such methods are based on the segregation of individual alleles in the spores produced by a desired plant and/or in the progeny derived from the self-pollination of that desired plant, and on the subsequent identification of suitable progeny plants in one generation, or in a limited number of inbred cycles. Such a method is known from WO2014076249 or from Wijnker et al, Nature Protocols Volume: 9, Pages: 761-772 (2014) DOI: doi: 10.1038/nprot.2014.049, which are enclosed by reference. Such method for producing parental lines for a hybrid organism, comprises the steps of: a) defining a set of genetic markers that are present in a heterozygous form (H) in a partially heterozygous starting organism; b) producing doubled haploid lines from spores of the starting organism: c) genetically characterizing the doubled haploid lines thus obtained for the said set of genetic markers to determine whether they are present in a first homozygous form (A) or in a second homozygous form (B); d) selecting at least one pair of doubled haploid lines that have complementary alleles for at least a subset of the genetic markers, wherein each member of the pair is suitable as a parental line for a hybrid organism.

Thus in one aspect, the invention relates to a method of producing a combination of parental lines of a plant of the invention (NUN 89849 CAC) comprising the step of making double haploid cells from haploid cells from the plant of the invention (NUN 89849 CAC) or a seed of that plant; and optionally crossing these parental lines to produce and collect seeds. In another aspect, the invention relates to a combination of parental lines produced by this method. In still another aspect said combination of parental lines can be used to produce a seed or plant of NUN 89849 CAC when these parental lines are crossed. In still another aspect, the invention relates to a combination of parental lines from which a seed or plant having all but one, two or three physiological and/or morphological characteristics of NUN 89849 CAC can be produced; or in another aspect, wherein a seed or plant having the distinguishing characteristics 1)-4) or 1)-7) of NUN 89849 CAC, as herein defined, can be produced when grown under the same environmental conditions. In still another aspect, the invention relates to a combination of parental lines from which a seed or plant having all the characteristics of NUN 89849 CAC as defined in Table 1 can be produced when grown under the same conditions.

All documents (e.g., patent publications) are herein incorporated by reference in their entirety.

CITED REFERENCES ams.usda.gov/AMSv1.0/getfile?dDocName=STELDEV3003780 http://www.rhs.org.uk/Plants/RHS-Publications/RHS-colour-charts http://www.upov.int/edocs/tgdocs/en/tg076.pdf Acquaah, Principles of Plant Genetics and Breeding, 2007, Blackwell Publishing, ISBN-13: 978-1-4051-3646-4

Arnholdt-Schmitt et al., 1995 Theor Appl Genet (1995) 91:809-815

Stein and Nothnagel, (1995) Plant Breeding 114, 1-11

Larkin and Scowcroft, (1981) Theor. Appl. Genet. 60, 197-214)

Jhang et al., J. Agricultural Sci. 2010—Vol 148 (2) pp 171-181

Shim and Jørgensen, Theor Appl Genet (2000) 101:227-233

Wijnker et al, Nature Protocols Volume: 9, Pages: 761-772 (2014) DOI: doi:10.1038/nprot.2014.049

US 2006/0168701

WO2014076249

Examples

Development of NUN 89849 CAC

The hybrid NUN 89849 CAC was developed from a male and female proprietary inbred line of Nunhems. The female and male parents were crossed to produce hybrid (F1) seeds of NUN 89849 CAC. The seeds of NUN 89849 CAC can be grown to produce hybrid plants and parts thereof (e.g. carrot root). The hybrid NUN 89849 CAC can be propagated by seeds or vegetative.

The hybrid variety is uniform and genetically stable. This has been established through evaluation of horticultural characteristics. Several hybrid seed production events resulted in no observable deviation in genetic stability. Coupled with the confirmation of genetic stability of the female and male parents the Applicant concluded that NUN 89849 CAC is uniform and stable.

DEPOSIT INFORMATION

A total of 2500 seeds of the hybrid variety NUN 89849 CAC were deposited according to the Budapest Treaty by Nunhems B.V. on Apr. 10, 2015, at the NCIMB Ltd., Ferguson Building, Craibstone Estate, Bucksburn, Aberdeen AB21 9YA, United Kingdom (NCIMB). The deposit has been assigned or NCIMB 42394. A deposit of NUN 89849 CAC and of the male and female parent line is also maintained at Nunhems B.V. Access to the deposit will be available during the pendency of this application to persons determined by the Director of the U.S. Patent Office to be entitled thereto upon request. Subject to 37 C.F.R. §1.808 (b), all restrictions imposed by the depositor on the availability to the public of the deposited material will be irrevocably removed upon the granting of the patent. The deposit will be maintained for a period of 30 years, or 5 years after the most recent request, or for the enforceable life of the patent whichever is longer, and will be replaced if it ever becomes nonviable during that period. Applicant does not waive any rights granted under this patent on this application or under the Plant Variety Protection Act (7 USC 2321 et seq.).

The most similar variety to NUN 89849 CAC is Nutri-Red, a commercial variety from Seminis. In Table 1 a comparison between NUN 89849 CAC and Nutri-Red is shown based on a trial in the USA. Trial location: Acampo California USA, (coordinates: 32.74520°N,-115.37179°W). Harvesting date for NUN 89849 was Feb. 11, 2015.

Two replications of 50 plants each, from which 15 plants or plant parts were randomly selected to measure characteristics. In Table 1 the USDA descriptors of NUN 89849 CAC (this application) and reference Nutri-Red (commercial variety) are summarized. In Table 2, additional descriptors of NUN 89849 CAC and Nutri-Red are summarized.

TABLE 1

| USDA descriptor | NUN 89849 | Nutri-Red |
|---|---|---|
| 1. TYPE | | |
| 1 = Amsterdam; 2 = Flakee; 3 = Berlicum; 4 = Chantenay; 5 = Danvers; 6 = Imperator; 7 = Nantes; 8 = Other (Specify) | 6/7 (Red) | 6 (Red Emperator) |
| 2, REGION OF ADAPTATION IN THE U.S.A.: | | |
| 1 = Northeast; 2 = Northwest; 3 = Southeast; 4 = Southwest; 5 = North Central; 6 = South Central; 7 = Most Regions | 7 | 7 |
| 3. MARKET MATURITY | | |
| No. Days from Seeding to Harvest | 110-140 | 110-140 |
| 4. PLANT TOP: (At Harvest Stage) | | |
| Habit: | 2 | 2 |
| 1 = Erect; 2 = Semi-erect; 3 = Prostrate | | |
| Plant Top Height (from Shoulder to Top of Crown) | 45.4 cm | 53.2 cm |
| Plant Top Neck Diameter | 10.2 mm | 18.8 mm |
| Top Attachment: | 1 | 1 |
| 1 = Single 2 = Multiple | | |
| 5. LEAF: (At Harvest Stage) | | |
| Name of Color Chart: RHS Colour Cart | 2 | 3 |
| Blade Color: 1 = Light Green; 2 = Medium Green; 3 = Dark Green; 4 = Other (Specify) | | |
| Color Chart Value | Green 137B | Green 137A |
| Blade Divisions: | 2 | 2 |
| 1 = Fine; 2 = Medium; 3 = Coarse | | |
| Blade Length (Without Petiole) | 18.6 cm | 23.9 cm |
| Petiole Length from Crown to First Pinna | 21.3 cm | 27.2 cm |
| Petiole Anthocyanin: | 1 | 1 |
| 1 = Absent; 2 = Present | | |
| Petiole Pubescence: | 1 | 1 |
| 1 = Absent; 2 = Present | | |
| 6. ROOT: (At Market Maturity) | | |
| Cortex Thickness (Midpoint X-Section) | 9.2 mm | 9.0 mm |
| Core Thickness (Midpoint X-Section) | 7.9 mm | 6.5 mm |
| Carrot Length (Minus Taproot) | 21.3 cm | 21.8 cm |
| Length of Taproot | 48.8 mm | 24.3 mm |
| Diameter at Shoulder | 29.2 mm | 27.4 mm |
| Diameter at Midpoint | 26.1 mm | 24.6 mm |
| Amount Exposed (Above Ground): 1 = None; 2 = 1-10%; 3 = 11-20%; 4 = 21-30%; 5 = 31-40%; 6 = >40% | 1 | 1 |
| Shape: | 2 | 2 |
| 1 = Round; 2 = Conic; 3 = Cylindrical | | |
| Collar: | 2 | 2 |
| 1 = Sunken; 2 = Level; 3 = Square | | |
| Shoulder: | 2 | 2 |
| 1 = Rounded; 2 = Sloping; 3 = Square | | |
| Base: | 2 | 1 |
| 1 = Pointed; 2 = Medium; 3 = Blunt | | |
| Surface Smoothness: | 2 | 2 |
| 1 = Very Smooth; 2 = Dimpled or Corrugated | | |

TABLE 1-continued

| USDA descriptor | NUN 89849 | Nutri-Red |
|---|---|---|
| Number of Secondary Root Scars: 1 = None; 2 = Few; 3 = Many | 2 | 2 |
| Appearance of Secondary Root Scars: 1 = Not Prominent; 2 = Prominent | 2 | 2 |
| Halo: 1 = None; 2 = Faint; 3 = Prominent | 2 | 2 |
| Zoning: 1 = None; 2 = Faint; 3 = Prominent | 3 | 2 |
| Flavor Harshness: 1 = Very Harsh; 2 = Moderately Harsh; 3 = Mildly Harsh | 3 | 1 |
| Flavor Sweetness: 1 = Not Sweet; 2 = Moderately Sweet; 3 = Very Sweet | 3 | 1 |
| COLORS: Color choices: 1 = white; 2 = yellow; 3 = orange; 4 = red; 5 = green; 7 = salmon; 8 = light; 9 = dark; 10 = other; color examples: 02 = yellow; 34 = orange-red; 94 = dark red | | |
| Name of Color Chart: | RHS Colour Chart | |
| Below Ground Exterior Color | | |
| Shoulder | 04: Greyed-red 181A | 84: Greyed-orange 175C |
| Skin | 04: Greyed-red 181A | 84: Greyed-orange 175C |
| X-Section Interior Color | | |
| Core | 04: Red 47A | 84: Greyed-orange 179B |
| Phloem | 04: Red 47A | 84: Greyed-orange 179B |
| 7. FLOWER | — | — |
| 8. DISEASE REACTIONS: (1 = Susceptible; 2 = Resistant; give races if known) | | |
| Root Knot Nematode | 1 | 1 |
| 9. INSECT REACTIONS: (1 = Susceptible; 2 = Resistant; give races if known) | — | — |
| 10. PHYSIOLOGICAL REACTIONS: (1 = Susceptible and 2 = Resistant) | | |
| Bolting | 2 | 2 |
| Root Splitting | 2 | 2 |

These are typical values. Values may vary due to environment. Other values that are substantially equivalent are also within the scope of the invention. N.A.=not applicable; n.r=not recorded.

The carrot weight, Brix and the leaf petiole diameter was also determined in NUN 89849 and in the most similar variety Nutri-Red (Table 2).

To determine weight, soil was removed from the mature, harvested roots and they were weighed on standard scales.

TABLE 2

| | NUN 89849 | Nutri-Red |
|---|---|---|
| Weight | 102.1 gram | 91.3 gram |
| Brix | 9.8 | 9.51 |
| Petiole diameter (leaf) | 3.5 mm | 4.7 mm |

These are typical values. Values may vary due to environment. Other values that are substantially equivalent are also within the scope of the invention.

The invention claimed is:

1. A plant, plant part or seed of carrot variety NUN 89849 CAC, wherein a representative sample of said seed has been deposited under Accession Number NCIMB 42394.

2. A plant or part thereof grown from the seed of claim 1.

3. The plant part of claim 2, further defined as a leaf, pollen, stem, an ovule, a root, a scion, a rootstock, cutting, flower or a part of any of these or a cell.

4. A *Daucus carota* plant, or a part thereof which does not differ from the plant of claim 2 in any of the distinguishing characteristics selected from Table 1.

5. A tissue or cell culture of regenerable cells of the plant of claim 2.

6. The tissue or cell culture according to claim 5, comprising cells or protoplasts from a plant part selected from the group consisting of embryos, meristems, cotyledons, hypocotyl, pollen, leaves, anthers, roots, root tips, taproots, pistil, petiole, flower, fruit, seed, stem and stalks.

7. A carrot plant regenerated from the tissue or cell culture of claim 5, wherein the plant has all of the physiological and morphological characteristics of the plant of claim 2 as listed in Table 1.

8. A method of producing of the plant of claim 2, or a part thereof, comprising vegetative propagation of the plant of claim 2.

9. The method of claim 8, wherein said vegetative propagation comprises regenerating a whole plant from a part of the plant of claim 2.

10. The method of claim 8, wherein said part is a cutting, a cell culture or a tissue culture.

11. A vegetative propagated plant of claim 2, or a part thereof, wherein the plant has all of the physiological and morphological characteristics of the plant of claim 2.

12. A method of producing a carrot plant, comprising crossing the plant of claim 2 with a second carrot plant one or more times, and selecting progeny from said crossing and optionally allowing the progeny to form seed.

13. A carrot plant having one, two or three physiological and/or morphological characteristics which is different from those of the plant of claim 2 and which otherwise has all the physiological and morphological characteristics of the plant of claim 2 as listed in Table 1.

14. A food or feed product comprising the plant part of claim 3 wherein the plant part can be identified as a part of NUN 89849 CAC, wherein a representative sample of said seed has been deposited under Accession Number NCIMB 42394.

15. A carrot plant comprising at least a first set of the chromosomes of the plant of claim 2.

16. A method of producing a combination of parental lines of the plant of claim 2 comprising the step of making double haploid cells from haploid cells from the plant of claim 2 or a seed of claim 1.

* * * * *